United States Patent
Israel et al.

[11] Patent Number: 5,972,018
[45] Date of Patent: *Oct. 26, 1999

[54] FLEXIBLE EXPANDABLE STENT

[75] Inventors: Henry Marshall Israel, Bnei Brak; Gregory Pinchasik, Ramat Hasharon, both of Israel

[73] Assignee: Medinol Ltd., Tel Aviv, Israel

[*] Notice: This patent is subject to a terminal disclaimer.

[21] Appl. No.: 09/026,099

[22] Filed: Feb. 19, 1998

Related U.S. Application Data

[63] Continuation of application No. 08/782,467, Jan. 10, 1997, abandoned, which is a continuation of application No. 08/457,354, May 31, 1995, Pat. No. 5,733,303, which is a continuation of application No. 08/282,181, Jul. 28, 1994, abandoned, and a continuation-in-part of application No. 08/213,272, Mar. 17, 1994, Pat. No. 5,449,373.

[51] Int. Cl.⁶ .................................................. A61M 29/00
[52] U.S. Cl. .............................. 606/198; 623/1; 623/12
[58] Field of Search .............................. 606/1, 108, 194, 606/195, 198, 200; 623/1, 12

[56] References Cited

U.S. PATENT DOCUMENTS

| | | |
|---|---|---|
| 4,733,665 | 3/1988 | Palmaz . |
| 4,762,128 | 8/1988 | Rosenbluth . |
| 4,800,882 | 1/1989 | Gianturco . |
| 4,830,003 | 5/1989 | Wolff et al. . |
| 4,856,516 | 8/1989 | Hillstead . |
| 4,886,062 | 12/1989 | Wiktor . |
| 4,922,905 | 5/1990 | Strecker . |
| 4,950,227 | 8/1990 | Savin et al. . |
| 4,969,458 | 11/1990 | Wiktor . |
| 4,994,071 | 2/1991 | MacGregor . |
| 5,019,085 | 5/1991 | Hillstead . |
| 5,019,090 | 5/1991 | Pinchuk . |
| 5,035,706 | 7/1991 | Giantureo . |
| 5,102,417 | 4/1992 | Palmaz . |
| 5,104,404 | 4/1992 | Wolff . |
| 5,116,365 | 5/1992 | Hillstead . |
| 5,133,732 | 7/1992 | Wiktor . |
| 5,158,548 | 10/1992 | MacGregor . |
| 5,161,547 | 11/1992 | Tower . |
| 5,195,984 | 3/1993 | Schatz . |
| 5,282,824 | 2/1994 | Gianturco . |
| 5,314,472 | 5/1994 | Fontaine . |
| 5,330,500 | 7/1994 | Song . |
| 5,354,308 | 10/1994 | Simon et al. . |
| 5,354,309 | 10/1994 | Schepp et al. . |
| 5,383,892 | 1/1995 | Cardon et al. . |
| 5,405,377 | 4/1995 | Cragg . |
| 5,441,515 | 8/1995 | Khosravi et al. . |
| 5,443,496 | 8/1995 | Schwartz et al. . |
| 5,449,373 | 9/1995 | Pinchasik et al. . |
| 5,507,767 | 4/1996 | Maeda et al. . |
| 5,540,712 | 7/1996 | Kleshinski et al. . |
| 5,554,181 | 9/1996 | Das . |
| 5,643,312 | 7/1997 | Fischell et al. . |
| 5,649,952 | 7/1997 | Lam . |
| 5,651,174 | 7/1997 | Schwartz et al. . |
| 5,653,727 | 8/1997 | Wiktor . |

FOREIGN PATENT DOCUMENTS

| | | |
|---|---|---|
| 0 335 341 | 4/1989 | European Pat. Off. . |
| 0 540 290 | 5/1993 | European Pat. Off. . |
| 0 541 443 | 5/1993 | European Pat. Off. . |
| 0 566 807 | 10/1993 | European Pat. Off. . |
| 0 606 165 | 7/1994 | European Pat. Off. . |
| WO 95/31945 | 11/1995 | WIPO . |
| WO 96/03092 | 2/1996 | WIPO . |

*Primary Examiner*—Michael Buiz
*Assistant Examiner*—William Lewis
*Attorney, Agent, or Firm*—Kenyon & Kenyon

[57] ABSTRACT

There is disclosed a stent for implanting in the body. The stent is formed of a tube having a patterned shape which has first and second meander patterns having axes extending in first and second directions. The first meander patterns can be formed into even and odd first meander patterns. The even and odd first meander patterns are 180° out of phase with each other and the odd patterns occur between every two even patterns. The second meander patterns are intertwined with the first meander patterns. The first and second directions can be orthogonal to each other. The second meander patterns can also be formed of even and odd patterns.

64 Claims, 6 Drawing Sheets

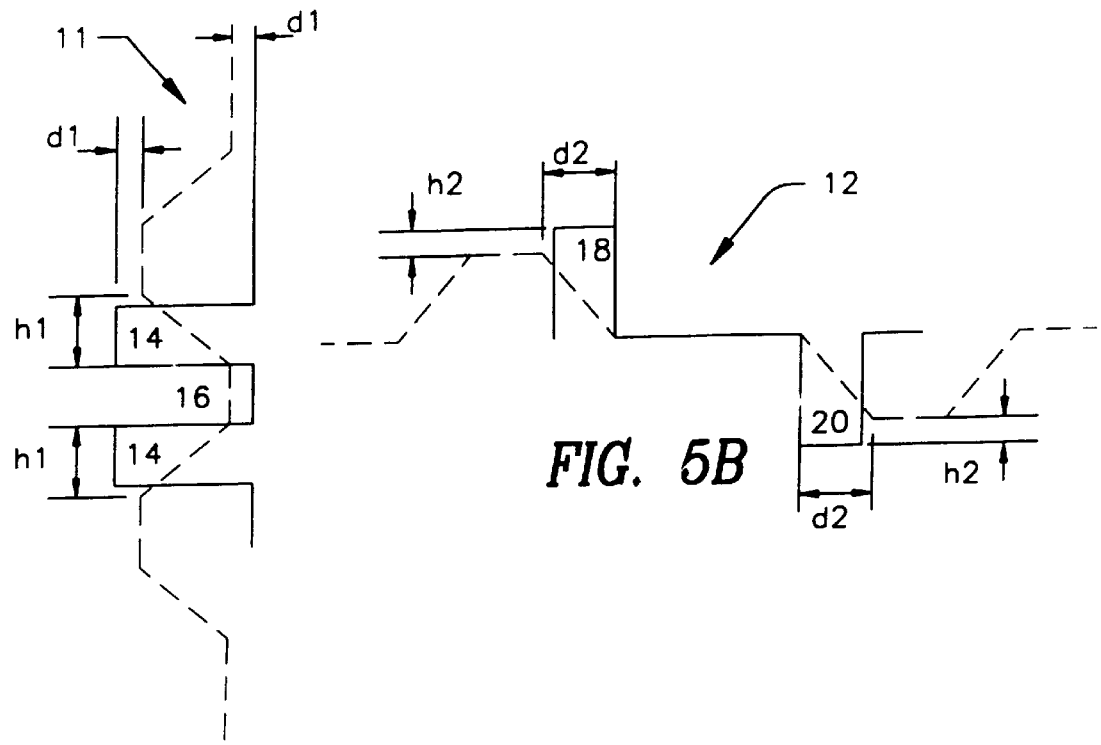
FIG. 5A
FIG. 5B
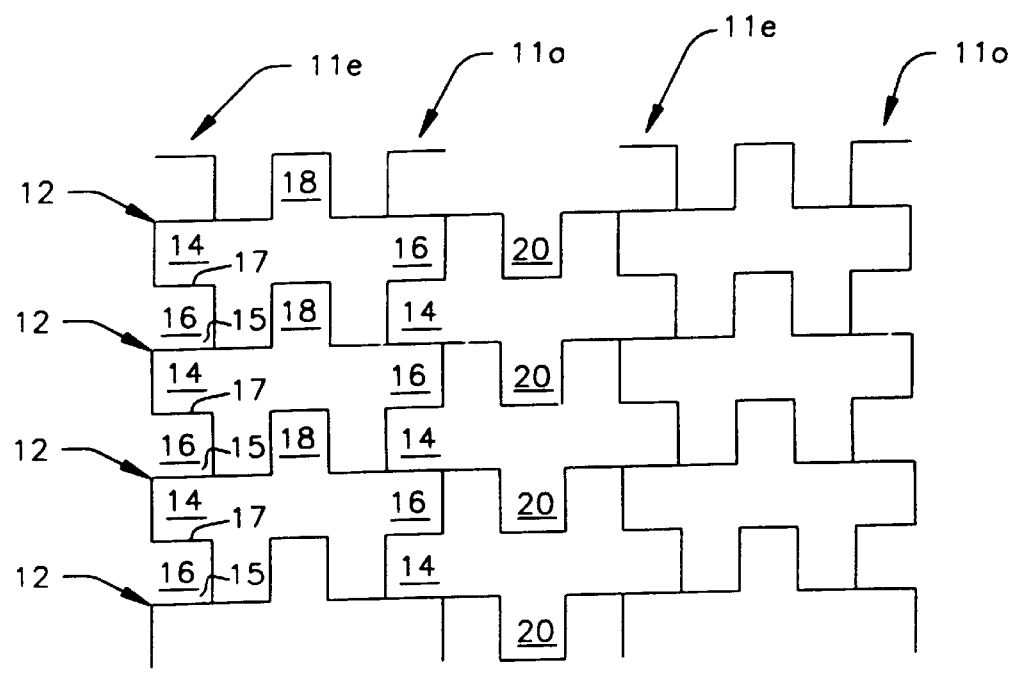
FIG. 6

FLEXIBLE EXPANDABLE STENT

This application is a continuation of Ser. No. 08/782,467 filed Jan. 10, 1997, now abandoned which is a continuation of Ser. No. 08/457,354, filed May 31, 1995 (now U.S. Pat. No. 5,733,303), which is a continuation of Ser. No. 08/282,181 filed Jul. 28, 1994 (now abandoned) and a continuation-in-part of Ser. No. 08/213,272, filed Mar. 17, 1994 (now U.S. Pat. No. 5,449,373).

BACKGROUND OF THE INVENTION

Various stents are known in the art wherein, for the present application, the term "stent" indicates a device, made of body-compatible material, which is utilized to widen a blood vessel, or other orifice in the body, and to maintain the resultant size of the lumen. Typically, the stent is delivered to the desired location in the body with an inflatable balloon and, when the balloon is inflated, the stent expands, thereby widening the orifice. Other mechanical devices which cause expansion of the stent are also utilized.

Exemplary patents in the field of stents formed of wire are: U.S. Pat. No. 5,019,090 to Pinchuk, U.S. Pat. No. 5,161,547 to Tower, U.S. Pat. No. 4,950,227 to Savin, et al., U.S. Pat. No. 5,314,472 to Fontaine, U.S. Pat. No. 4,886,062 and U.S. Pat. No. 4,969,458 to Wiktor and U.S. Pat. No. 4,856,516 to Hillstead. Stents formed of cut stock metal are described in: U.S. Pat. No. 4,733,665 to Palmaz, U.S. Pat. No. 4,762,128 to Rosenbluth, U.S. Pat. No. 5,102,417 to Palmaz and Schatz, U.S. Pat. No. 5,195,984 to Schatz and WO 91FR013820 to Meadox.

The stents described in U.S. Pat. No. 5,102,417 to Palmaz and Schatz have expandable tubular grafts connected together with a flexible connector. The grafts are formed of a plurality of slots disposed parallel to the longitudinal axis of the tube. The flexible connectors are helical connectors. Since the tubular grafts are relatively rigid, the flexible connectors are needed so that the stents can bend when being fed through a curved blood vessel. When the stents of U.S. Pat. No. 5,102,417 expand, the grafts expand radially and, consequently, shrink longitudinally. However, at the same time, the helical connectors twist. The twisting motion is most probably harmful to the blood vessel.

U.S. Pat. No. 5,195,984 to Schatz describes a similar stent but with one straight connector, parallel to the longitudinal axis of the tubular grafts, between tubular grafts. The straight member removes the twisting motion; however, it is not a very strong connector.

SUMMARY OF THE PRESENT INVENTION

It is therefore an object of the present invention to provide a flexible stent which minimally shrinks, in the longitudinal direction, during expansion.

The stent of the present invention is formed of a tube having a patterned shape which has first and second meander patterns having axes extending in first and second directions wherein the second meander patterns are intertwined with the first meander patterns. The first and second directions can be orthogonal to each other.

In accordance with one embodiment of the present invention, the first meander patterns are formed into even and odd first meander patterns. The even and odd first meander patterns are 180° out of phase with each other and the odd patterns occur between every two even patterns. The second meander patterns can also be formed of even and odd patterns.

Additionally, in accordance with a preferred embodiment of the present invention, the second meander patterns have two loops per period and the even and odd first meander patterns are connected on first and second sides, respectively, of each loop of the second meander patterns.

Alternatively or in addition, the second meander patterns are formed of even and odd second meander patterns. In this embodiment, the even and odd first meander patterns have loops and the even and odd second meander patterns are connected to the even and odd first meander patterns so as to leave one full loop between each pair of even and odd second meander patterns.

Moreover, in accordance with a preferred embodiment of the present invention, the first and second meander patterns are formed from flat metal. Alternatively, they can be cut from wire. Further, they can be imbedded or covered with any body-compatible material.

BRIEF DESCRIPTION OF THE DRAWINGS

The present invention will be understood and appreciated more fully from the following detailed description taken in conjunction with the drawings in which:

FIGS. 5A and 5B are illustrations of the changes in the patterns of the stent of FIG. 1 due to expansion;

FIG. 6 is a schematic illustration of a second embodiment of the pattern for a stent;

DETAILED DESCRIPTION OF PREFERRED EMBODIMENTS

Figure 1:
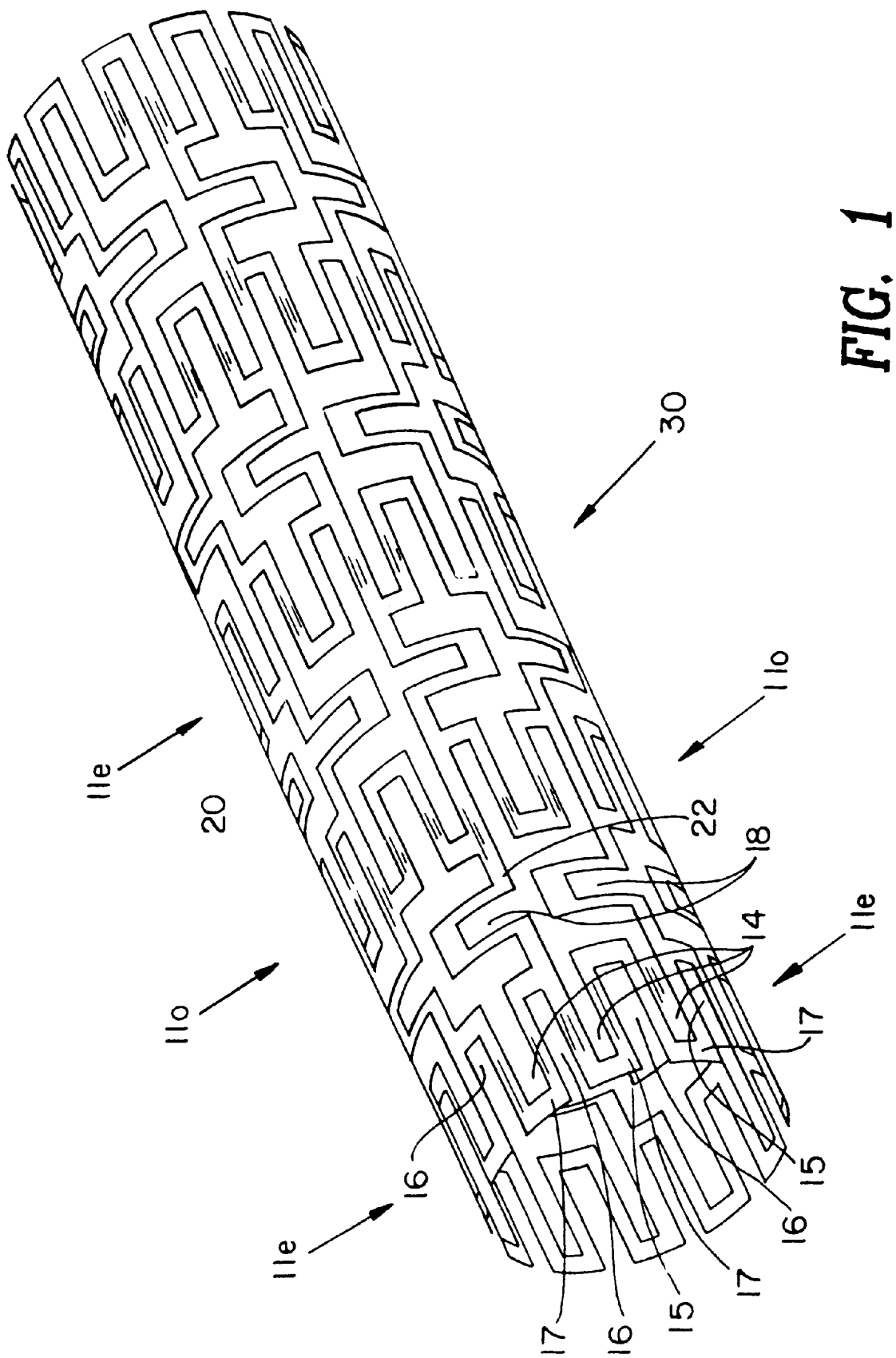
FIG. 1 is an illustration of a patterned stent, constructed and operative in accordance with a first preferred embodiment of the present invention.
Figure 2:
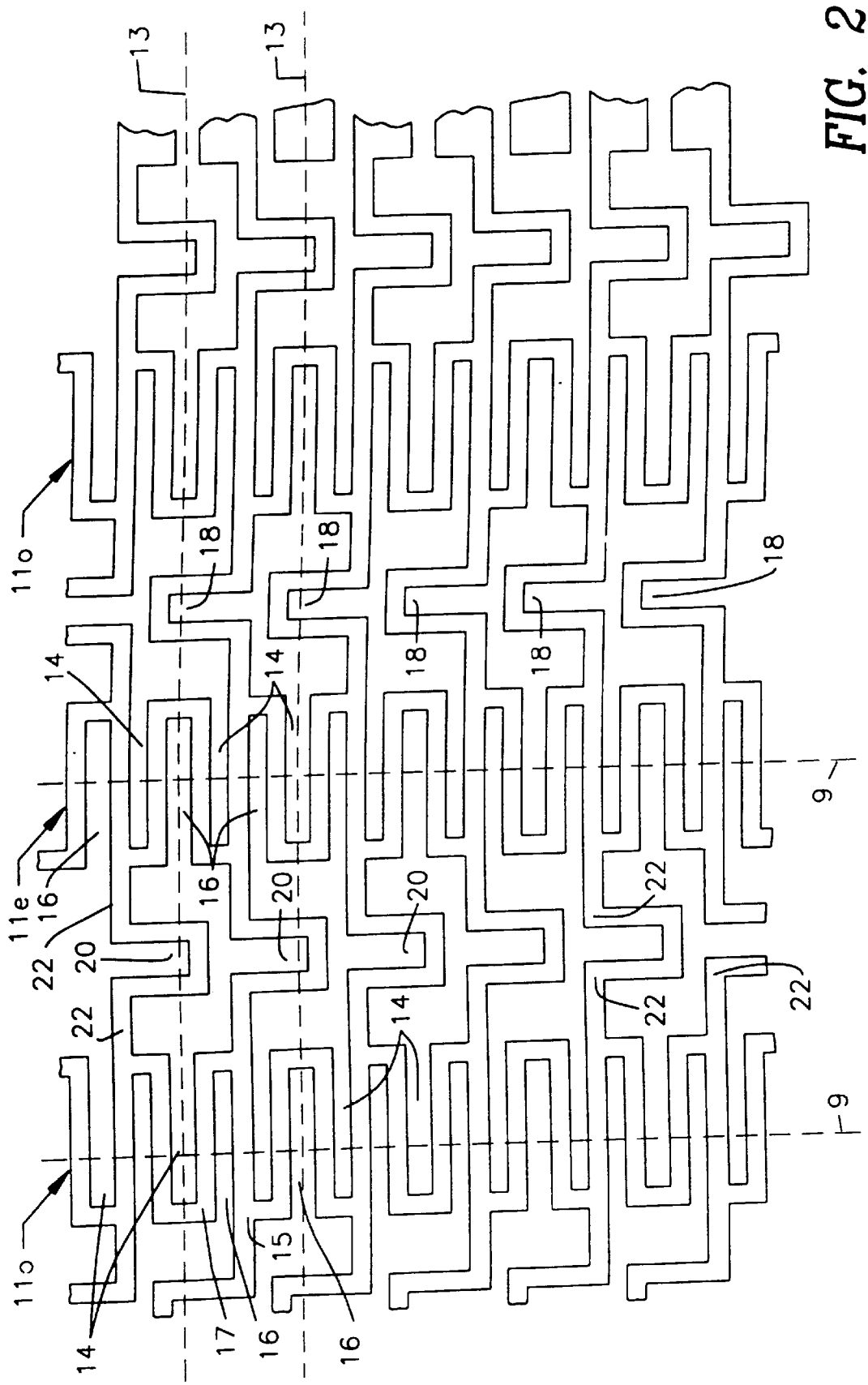
FIG. 2 is an illustration of the pattern of the stent of FIG. 1.
Figure 3:
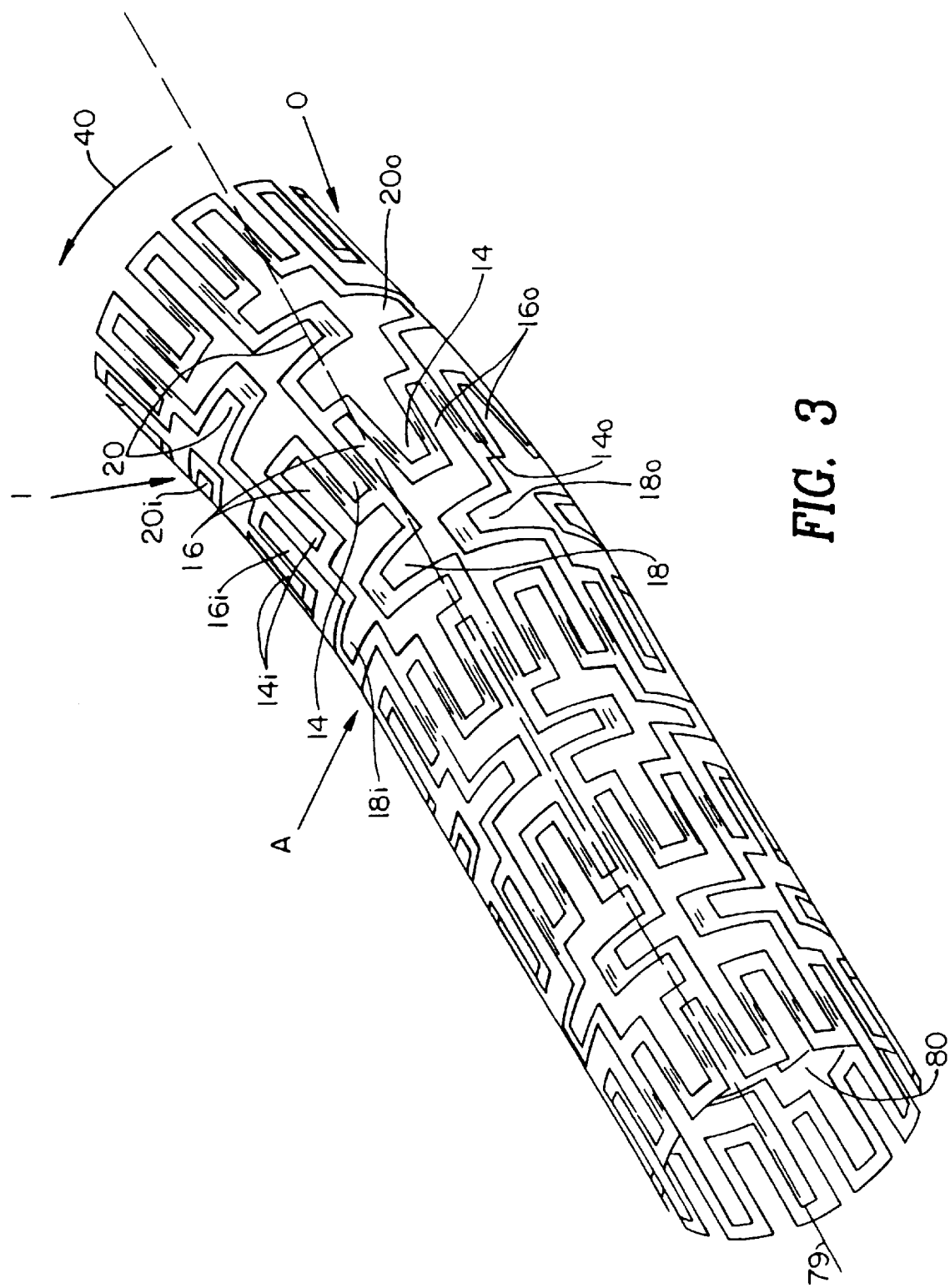
FIG. 3 is an illustration of the stent of FIG. 1 in a bent position.
Figure 4:
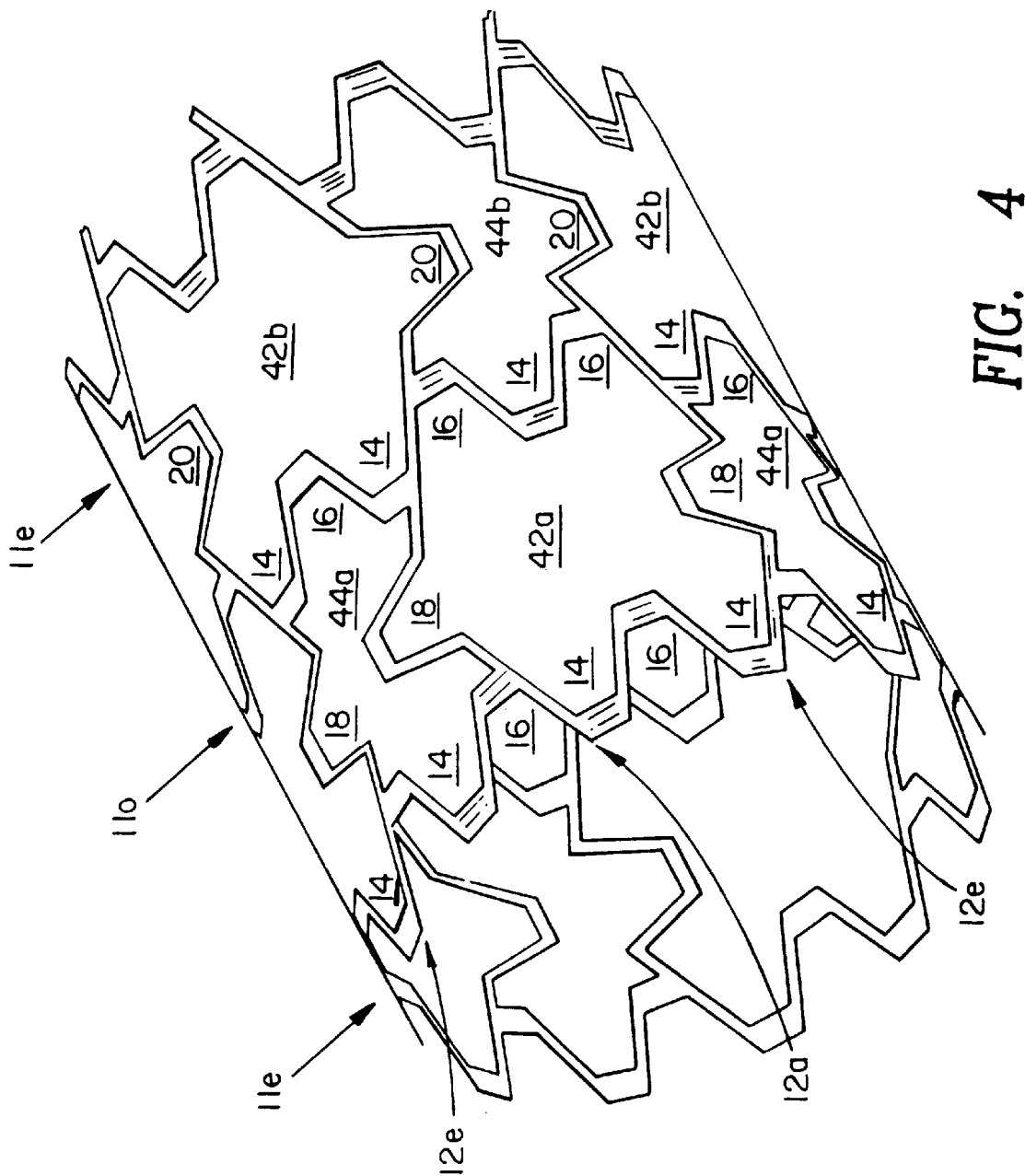
FIG. 4 is an illustration of the stent of FIG. 1 in an expanded format.

Reference is now made to FIGS. 1–4 which illustrate a first embodiment of a stent, constructed and operative in accordance with the principles of the present invention. FIG. 1 illustrates the stent in its non-expanded form, FIG. 2 illustrates the pattern of the stent, FIG. 3 illustrates it in a partially bent position and FIG. 4 illustrates it in an expanded form. As shown in FIG. 3, the stent 30 defines a longitudinal aperture 80 having a longitudinal axis or longitudinal extension 79.

The stent of the present invention is a tube whose sides are formed into a plurality of each of two orthogonal meander patterns which patterns are intertwined with each other. The term "meander pattern" is taken herein to describe a periodic pattern about a center line and "orthogonal meander patterns" are patterns whose center lines are orthogonal to each other.

In the stent of FIGS. 1–4, the two meander patterns are labeled 11 and 12 and they are most easily seen in FIG. 2. Meander pattern 11 is a vertica sinusoid having a vertical center line 9. Meander pattern 11 has two loops 14 and 16 per period wherein loops 14 open to the right while loops 16 open to the left. Loops 14 and 16 share common members 15 and 17, where (member 15) connects from one loop 14 to its following loop 16 and member 15 connects from one loop 16 to its following loop 14.

Meander pattern 12 is an horizontal pattern having an horizontal center line 13. Meander pattern 12 also has loops labeled 18 and 20, but between loops of a period is an extended straight section labeled 22. Loops 18 open downwards and loops 20 open upwards.

Vertical meander pattern 11 is provided in odd and even (o and e) versions which are 180° out of phase with each other. Thus, each left opening loop 16 of meander pattern 11o faces a right opening loop 14 of meander pattern 11e and a right opening loop 14 of meander pattern 11o faces a left opening loop 16 of meander pattern 11e.

Horizontal meander pattern 12 is also provided in odd and even forms. The straight sections 22 of horizontal meander pattern 12e intersect with every third common member 17 of vertical meander pattern 11e. The straight sections 22 of horizontal meander pattern 12o intersect with every third common member 15 of vertical meander patter 11e, beginning with the common member 15 two after an intersected common member 17. The result is a full loop 14 between meander patterns 12e and 12o and a full loop 16 between meander patterns 12o and 12e.

Returning to FIG. 1, the pattern of FIG. 2 is formed into a tube 30 of an easily deformable material, such as a metal. Due to the two meander patterns, the stent of FIG. 1, when attached over a catheter balloon, is flexible and can therefore be easily dragged through curved blood vessels. An example of the way in which the stent of FIG. 1 bends is illustrated in FIG. 3.

In FIG. 3, the stent begins to bend at the point marked A in the direction marked by arrow 40. As the stent begins to curve, the section marked 1 becomes the inside of the curve while the second marked O becomes the outside of the curve. The inside of the curve 1 is shortened vis-a-vis the outside of the curve O.

During bending, the loops 14–20 to the right of the point A change shape in order to compensate for the differences in length between the inside and outside curves. For example, loops 18i and 20i near the inside of the curve are closer together than loops 18o and 20o on the outside of the curve, which expand. Loops 14i and 16i near the inside I are compressed while the loops 14o and 16o closer to the outside O of the curve are expanded.

As can be seen, both meander patterns 11 and 12 are involved in the bending. Although not shown, it will be appreciated that the stent of FIGS. 1–4 can bend in any direction and in more than one direction at any time.

FIG. 4 illustrates the stent of FIG. 1 in its expanded form. When the stent expands, both meander patterns 11 and 12 expand (i.e. all loops 14–20 open up). As can be seen, the expanded stent has two types of enclosed spaces, a large space 42 between meander patterns 12o and 12e and a small space 44 between meander patterns 12e and 12o. As can also be seen, each large space 42 has two loops 14 on its left side and two loops 16 on its right side. The large spaces between vertical meander patterns 11e and 11o, which are labeled 42a, have loops 18 at their tops and bottoms while the large spaces between vertical meander patterns 11o and 11e, which are labeled 42b, have loops 20 at their tops and bottoms. Similarly for small spaces 44a and 44b.

It is noted that, due to the orthogonal meander patterns 11 and 12, the stent of FIG. 1 does not significantly shrink during expansion. This is illustrated in detail in FIGS. 5A and 5B to which reference is now made. FIG. 5A illustrates the movement, during expansion, of one vertical meander pattern 11 and FIG. 5B illustrates the movement, during expansion, of one horizontal meander pattern 12. The original patterns are shown with solid lines and the expanded patterns are shown with dashed lines.

The vertical meander pattern 11 of FIG. 5A expands by widening its loops 14 and 16. As a result, the vertical meander pattern 11 grows vertically by an amount $2*h_1$ per loop. However, it also shrinks horizontally, by an amount $2*d_1$. Similarly, the horizontal meander pattern 12 of FIG. 5B expands by widening its loops 18 and 20. As a result, the horizontal meander pattern 12 grows horizontally by an amount $2*d_2$ per loop. However, it also shrinks vertically, by an amount $h_2$. Thus, the vertical growth of the vertical meander pattern 11 compensates, at least partially, for the vertical shrinkage of the horizontal meander pattern 12, and vice versa. It is noted that the end portions of any stent are only partially compensated and therefore, may shrink somewhat.

It will be appreciated that the two orthogonal meander patterns 11 and 12 and the compensation they provide to each other provides flexibility to the unexpanded stent of FIG. 1. However, when the stent is expanded, the changes in each of loops 14 and 16 provide rigidity to the resultant stent and thus, enable the stent to maintain a blood vessel at a desired inner diameter.

The stent of the present invention can be manufactured from flat metal which is etched into the pattern of FIG. 2. The etched metal is then bent to form the tube 30. Alternatively, the pattern of FIG. 2 can be manufactured from welded or twisted wire.

It will be appreciated that the stent of the present invention can be made form metal and/or wire. Additionally, it can be plated with a protective material, embedded with a medicine, and/or covered with a material which can fill in the spaces 42 and 44.

Figure 7:
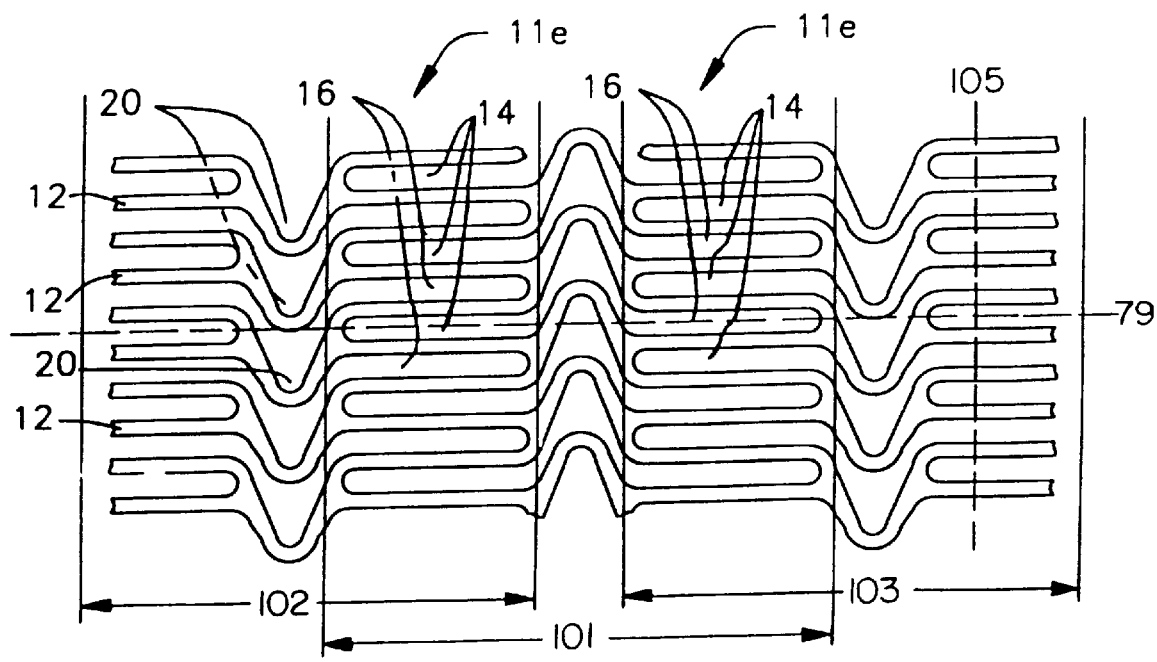
FIG. 7 is an illustration of a third embodiment of the pattern for the stent.
Figure 8:
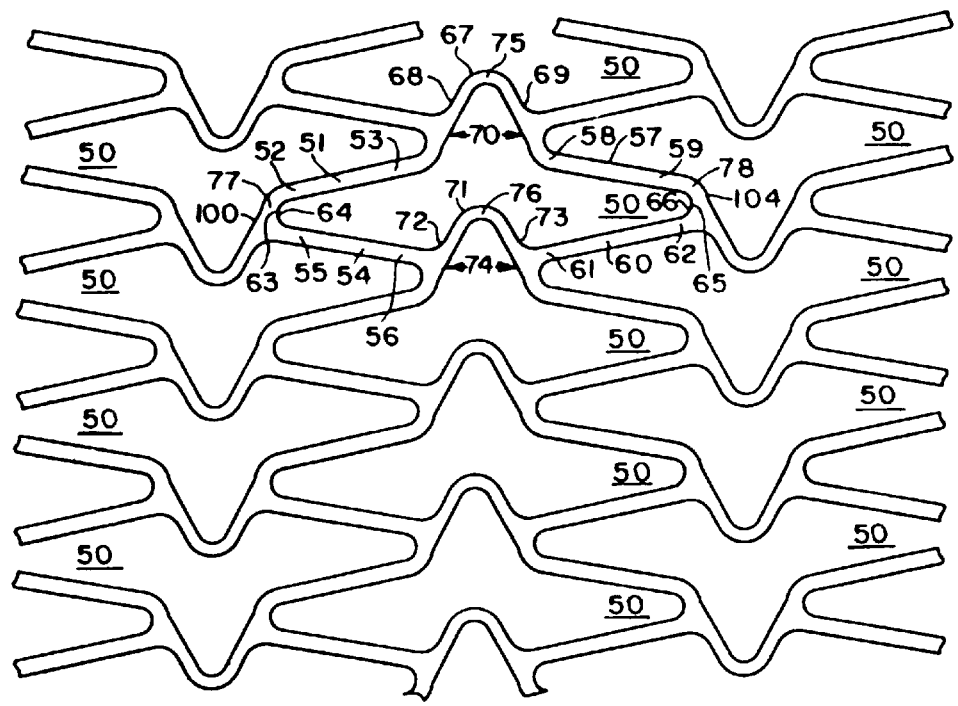
FIG. 8 is an illustration of the pattern of FIG. 7 in an expanded format.

It will be appreciated that the present invention encompasses all stents manufactured with a pattern formed of two meander patters, orthogonal or otherwise. Another exemplary pattern, also with orthogonal meander patters, is provided herein wherein FIG. 6 is a schematic version and FIG. 7 is a more rounded version. FIG. 8 shows the pattern of FIG. 7 in an expanded format. The pattern of FIGS. 6 and 7 is similar to that shown in FIG. 2 except that it has more horizontal meander patterns 12 and they are of one kind, rather than being even and odd as in FIG. 2.

As can be seen in both FIGS. 6 and 7, there are two types of vertical meander patters 11e and 11o which are 180° out of phase with each other. The horizontal meander patterns 12 connect with every line 15 of vertical meander pattern 11e.

FIG. 8 illustrates the pattern of FIG. 7 is an expanded format. Since there are no even and odd horizontal meander patterns, in the expanded format of FIG. 8, there are no large and small spaces. Instead, all spaces are of the same size, i.e., the stent is comprised of a plurality of spaces or cells 50 defining a uniform cellular structure.

As shown in FIGS. 3, 7 and 8, Applicants' invention can also be described as an expandable stent defining a longitudinal aperture 80 having a longitudinal axis or extension 79 and a circumferential axis or extension 105, including a plurality of flexible connected cells 50 with each of the flexible cells 50 having a first longitudinal end 77 and a second longitudinal end 78. Each cell 50 also is provided with a first longitudinal apex 100 disposed at the first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop 63 defining a first angle 64 disposed between the first end 52 of the first member 51 and the first end 55 of the second member 54. A second loop 65 defining a second angle 66 is disposed between the second end 59 of the third member 57 and the second end 62 of the fourth member 60 and is disposed generally opposite to the first loop 63. A first flexible compensating member or flexible link 67 having a first end 68 and a second end 69 is disposed between the first member 51 and the third member 57 with the first end 68 of the first flexible compensating member or flexible link 67 communicating with the second end 53 of the first member 51 and the second end 69 of the first flexible compensating member or flexible link 67 communicating with the first end 58 of the third member 57. The first end 68 and the second end 69 are disposed a variable longitudinal distance 70 from each other. A second flexible compensating member 71 having a first end 72 and a second end 73 is disposed between the second member 54 and the fourth member 60. The first end 72 of the second flexible compensating member or flexible link 71 communicates with the second end 56 of the second member 54 and the second end 73 of the second flexible compensating member or flexible link 71 communicates with the first end 61 of the fourth member 60. The first end 72 and the second end 73 are disposed a variable longitudinal distance 74 from each other. In a preferred embodiment, the first and second flexible compensating member or flexible links 67 and 71 are arcuate. The fist and second flexible compensating member or flexible links 67 and 71 are differentially extendable or compressible when the stent is bent in a curved direction away from the longitudinal axis 79 of the aperture 80. (Shown in FIG. 3.) The first member 51, second member 54, third member 57, and fourth member 60 and the first loop 63 and the second loop 65 and the first flexible compensating member or flexible link 67 and the second flexible compensating member or flexible link 71 are disposed so that as the stent is expanded the distance between the first flexible compensating member or flexible link 67 and the second flexible compensating member or flexible link 71 increases and the longitudinal component of the first member 51, second member 54, third member 57 and fourth member 60 decreases while the first loop 63 and the second loop 65 remain generally opposite to one another, the ends 68 and 69 of the first flexible compensating member or flexible link 67 and the ends 72 and 73 of the second flexible compensating member or flexible link 71 open so as to increase the variable longitudinal distance 70 between the first end 68 and the second end 69 of the first flexible compensating member or flexible link 67 and so as to increase the variable longitudinal distance 74 between the first end 72 and the second end 73 of the second flexible compensating member or flexible link 71. This compensates for the decreasing of the longitudinal component of the first member 51, second member 54, third member 57, and fourth member 60 and substantially lessens the foreshortening of the stent upon its expansion. In a preferred embodiment, and as shown in FIG. 5A, the flexible compensating member or flexible links 67 and 71 compensate in an amount that is substantially equal to the amount that the stent foreshortens. As shown in FIGS. 7 and 8, the first flexible compensating member or flexible link 67 and the second flexible compensating member or flexible link 71 in each cell 50 of each row or band of cells 101, 102 and 103, serve to flexibly connect other cells 50 in adjacent rows or bands 102, 103, and 104 which themselves have first and second compensating members 67 and 71. As shown in FIG. 7, the first flexible compensating member or flexible links 67 and 71 in row or band 101 serve to flexibly connect the cells 50 in adjacent rows or bands 102 and 103. As shown in FIGS. 7 and 8, a portion of the flexible member 67 or 71 disposed between the first ends 68 and 72 and the second ends 69 and 73 may be provided with a width that is smaller than the width of the apices 100 and 104 to which they are attached.

It will be appreciated by persons skilled in the art that the present invention is not limited to what has been particularly shown and described hereinabove. Rather the scope of the present invention is defined by the claims which follow:

We claim:

1. A stent formed of a tube having a patterned shape the patterned shape comprising:
    a) even first meander patterns having axes extending in a first direction;
    b) odd first meander patterns, also having axes extending in said first direction, wherein said odd first meander patterns are 180° out of phase with said even first meander patterns and occur between every two even first meander patterns;
    c) second meander patterns having axes extending in a second direction different than said first direction, wherein said second meander patterns are intertwined with said even and odd first meander patterns;
    d) wherein said first and said second meander patterns comprises loops;
    e) wherein said even and odd first meander patterns are connected on first and second sides, respectively, of each loop of said second meander patterns to said second meander patterns;
    f) wherein said second meander patterns are of one kind; and
    g) wherein said second meander patterns are connected to said even and odd first meander patterns so as to leave two loops of said first meander patterns between each pair of said second meander patterns.

2. A stent formed of a tube having a patterned shape, the patterned shape comprising:
    a) even first meander patterns having axes extending in a first direction;
    b) odd first meander patterns, also having axes in said first direction, wherein said odd first meander patterns are 180° out of phase with said even flat meander patterns and occur between every two even first meander patterns;
    c) second meander patterns having axes extending in a second direction different than said first direction, wherein said second meander pattern are intertwined with said even and odd first meander pattern;
    d) wherein said first and said second meander patterns comprise loops;
    e) wherein said even and odd first meander patterns are connected on first and second sides, respectively, of each loop of said second meander patterns to said second meander patterns;
    f) wherein said second meander patterns are formed of even and odd second meander patterns and are connected to said even and odd first meander patterns so as to leave three loops of said first meander patterns between each pair of said even and odd second meander patterns.

3. A stent according to claim 1 wherein said first and second directions are orthogonal.

4. A stent according to claim 1 wherein said first and second directions are not orthogonal.

5. An expandable stent in the shape of an elongated unitary tube formed from flat metal having a flexible patterned shape suitable for insertion into a blood vessel or other orifice in the body in which it may be expanded to maintain the resultant size of the lumen comprising: a plurality of first meander patterns extending in a first direction and a plurality of second meander patterns extending in a second direction, said meander patterns being connected together to form a plurality of flexible cells so that when attached to a balloon catheter the stent easily passes through the curved blood vessels, each of said flexible cells being provided with a plurality of loops adapted to cooperate so that upon the expansion of said stent the growth of some of said loops in the longitudinal direction of the tube compensates for the shrinkage of other loops in the longitudinal direction of the tube to eliminate any significant shrinkage of the stent in length during expansion.

6. A stent according to claim 5 wherein changes in the shape of the loops provide rigidity to the stent upon expansion to enable the stent to maintain a blood vessel or lumen at a desired inner diameter.

7. A stent according to claim 6 wherein the flexible cells of said stent are formed from orthogonal intertwined first and second meander patterns.

8. A stent according to claim 5 wherein the flexible cells of said stent are formed from intertwined circumferential and longitudinal meander patterns, and wherein upon expansion the circumferential growth of the circumferential meander pattern compensates, at least partially, for the circumferential shrinkage of the longitudinal meander pattern and vice versa.

9. A stent according to claim 8 wherein the end portions of said stent shrink somewhat upon expansion.

10. A flexible, expandable stent in the form of an elongated unitary tube comprising: a pattern which defines substantially uniform spaces or cells cut from flat metal, said stent adapted so that when it is expanded radially, its overall length remains substantially the same because some cell elements of the stent grow in the tube's longitudinal direction while some cell elements of the stent shrink in the tube's longitudinal direction.

11. An expandable stent in the shape of an elongated unitary tube formed of flat metal having a flexible patterned shape suitable for insertion into a blood vessel or other orifice in the body in which it may be expanded to maintain the resultant size of the lumen comprising: a plurality of first meander patterns extending in a first direction and a plurality of second meander patterns extending in a second direction, said meander patterns being connected together to form a plurality of flexible cells so that when attached to a balloon catheter the stent easily passes through the curved blood vessels, each of said flexible cells being provided with a plurality of loops, said loops adapted to cooperate so that upon bending of the stent the inside curvature is shortened with respect to the outside curvature and the loops change shape to compensate for the difference in length between the inside and outside curves.

12. A stent according to claim 11 wherein changes in the shape of the loops provides rigidity to the stent upon expansion to enable the stent to maintain a blood vessel or lumen at a desired inner diameter.

13. A stent according to claim 11 wherein the flexible cells of said stent are formed from orthogonal intertwined first and second meander patterns.

14. A stent according to claim 11 wherein the flexible cells of said stent are formed of intertwined circumferential and longitudinal meander patterns, each of which are involved in the bending of the stent.

15. A stent according to claim 14 wherein said stent can bend in any direction and in more than one direction at any time.

16. A flexible, expandable stent comprising: an elongated unitary tube formed of a pattern which defines spaces or cells cut from flat metal, said spaces or cells adapted to cooperatively change shape when the stent is bent, each of said uniform spaces or cells being adapted to facilitate either longitudinal expansion or shrinkage in order to accommodate the stent's bending.

17. A flexible, expandable stent comprising: an elongated unitary tube formed of a pattern which defines spaces cut from flat metal, said spaces or cells to cooperatively change shape when the stent is bent so that the spaces or cells nearer the inside of the curve shrink and the spaces near the outside of the curve grow, said cooperation enabling the stent to bend uniformly along its length.

18. A stent formed of a tube having a patterned shape, comprising:
  a) even first meander patterns, having axes extending in a first direction;
  b) odd first meander patterns, also having axes extending in said first direction, wherein said odd first meander patterns are 180° out of phase with said even first meander patterns and occur between every two even first meander patterns;
  c) second meander patterns having axes extending in a second direction different from said first direction, wherein said second meander patterns are intertwined with said even and odd first meander patterns to form a distributed structure;
  d) wherein said first and said second meander patterns comprise loops;
  e) wherein said even and odd first meander patterns are connected to said second meander patterns so as to leave a loop of said second meander patterns between each odd and even first meander patterns; and
  f) wherein said second meander patterns are connected to said even and odd first meander patterns so as to leave loops of said first meander patterns between each pair of second meander patterns.

19. A stent according to claim 18, wherein said second meander patterns are connected to said even and odd first meander patterns so as to leave two loops of said first meander patterns between each pair of second meander patterns.

20. A stent according to claim 18, wherein said second meander patterns are formed of even and odd second meander patterns and are connected to said even and odd first meander patterns so as to leave three loops of said first meander patterns between each pair of said even and odd second meander patterns.

21. A stent, according to claim 18, wherein said first and second directions are orthogonal.

22. A stent according to claim 18, wherein said first and second directions are not orthogonal.

23. A stent according to claim 18, wherein said first and second meander patterns are formed from wire.

24. A stent according to claim 18, wherein said first and second meander patterns are cut from flat metal.

25. A stent according to claim 18, wherein said stent is plated with a protective material embedded with medicine, and covered with a material.

26. A cylindrical stent, comprising:
(a) a plurality of odd and even alternating circumferential meanders, each substantially equally spaced from the next and each having alternate oppositely facing first areas of inflection, wherein the odd meanders are out of phase from the even meanders such that alternate first areas of inflection on the odd meanders are adjacent oppositely facing alternate first areas of inflection on the even meanders; and
(b) means connecting the odd and even meanders comprising a plurality of flexible links connecting adjacent first areas of inflection of adjacent even and odd meanders, wherein each flexible link has at least two portions connected by at least one second area of inflection, and wherein the first areas of inflection define a series of identical first bends and the second areas of inflection define a series of identical second bends; and wherein the bisecting lines of the first bends are at angles to the bisecting lines of the second bends.

27. A stent according to claim 26, wherein the meanders extend in the circumferential direction of the stent such that the bisecting lines of the first areas of inflection extend in the axial direction of the stent.

28. A stent according to claim 27, wherein the bisecting lines of the second areas of inflection extend in the circumferential direction of the stent.

29. A stent according to claim 28, wherein a flexible link connects each pair of adjacent first areas of inflection.

30. A stent according to claim 29, wherein the meanders and flexible links of the stent define a plurality of enclosed spaces; each enclosed space being defined by two first areas of inflection alternating with two flexible links.

31. A stent comprising:
a) at least odd and even alternating serpentine sections, each having first areas of inflection, wherein said odd serpentine section is out of phase from said even serpentine section such that first areas of inflection of said odd serpentine section are adjacent first areas of inflection on said even serpentine section; and
b) at least one flexible connector, comprising a plurality of flexible links connecting adjacent first areas of inflection of adjacent even and odd serpentine sections; wherein each flexible link has at least two portions connected by at least one second areas of inflection define first and second angles whose bisecting lines are at angles one to another.

32. A stent comprising a mesh of adjacent, connected cells, each cell comprising:
an even number of fixed length, alternating, first and second loops, connected together in a closed cell, each loop having at least two portions with an area of inflection there between, said first and second loops defining first and second angles whose bisecting lines are at angles one to another.

33. A flexible, expandable stent, comprising:
a plurality of flexible cells provided with a plurality of first loops and a plurality of second loops, said first loops and said second loops disposed and adapted to cooperate so that upon the expansion of said stent the vertical growth of said first loops substantially compensates for the vertical shrinkage of said second loops.

34. A flexible, expandable stent, comprising:
a plurality of first meander patterns extending in a first direction and a plurality of second meander patterns extending in a second direction intersecting said first meander patterns to define a plurality of enclosed cells, said first and said second meander patterns disposed and adapted to cooperate so that upon the expansion of said stent the vertical growth of said first meander patterns substantially compensates for the vertical shrinkage of said second meander patterns.

35. A flexible, expandable stent, comprising:
a plurality of flexible cells provided with a plurality of first loops and a plurality of second loops, said first loops and said second loops disposed and adapted to cooperate so that upon the expansion of said stent said first loops and said second loops change shape to compensate for the tendency of said stent to foreshorten when said stent is expanded.

36. A flexible, expandable stent, comprising:
a plurality of first meander patterns extending in a first direction and a plurality of second meander patterns extending in a second direction intersecting said first meander patterns to define a plurality of enclosed cells, said first and said second meander patterns disposed and adapted to cooperate so that upon the expansion of said stent said first meander patterns and said second meander patterns change shape to compensate for the tendency of said stent to foreshorten when said stent is expanded.

37. A flexible, expandable stent having a longitudinal axis, comprising:
a plurality of flexible cells provided with a plurality of first loops and a plurality of second loops, said loops adapted so that said stent prior to expansion is substantially uniformly flexible along its longitudinal axis and bendable in substantially any direction and in several directions at once without affecting the structural or functional integrity of said stent, said first loops and said second loops disposed and adapted to cooperate so that upon the expansion of said stent the vertical growth of said first loops substantially compensates for the vertical shrinkage of said second loops, said loops further adapted to impart rigidity to said stent in an amount sufficient to support a lumen when said stent is expanded.

38. A flexible, expandable stent having a longitudinal axis, comprising:
a plurality of first meander patterns extending in a first direction and a plurality of second meander patterns extending in a second direction intersecting said first meander patterns to define a plurality of enclosed cells, said meander patterns adapted so that said stent prior to expansion is substantially uniformly flexible along its longitudinal axis and bendable in substantially any direction and in several directions at once without affecting the structural or functional integrity of said stent, said first and said second meander patterns disposed and adapted to cooperate so that upon the expansion of said stent the vertical growth of said first meander patterns substantially compensates for the vertical shrinkage of said second meander patterns, said meander patterns further adapted to impart rigidity to said stent in an amount sufficient to support a lumen when said stent is expanded.

39. A flexible, expandable stent having a longitudinal axis, comprising:
a plurality of flexible cells provided with a plurality of first loops and a plurality of second loops, said loops adapted so that said stent prior to expansion is substantially uniformly flexible along its longitudinal axis and bendable in substantially any direction and in several directions at once without affecting the structural or functional integrity of said stent, said first loops and said second loops disposed and adapted to cooperate so that upon the expansion of said stent said first loops and said second loops change shape to compensate for the tendency of said stent to foreshorten when said stent is expanded, said loops further adapted to impart rigidity to said stent in an amount sufficient to support a lumen when said stent is expanded.

40. A flexible, expandable stent having a longitudinal axis, comprising:
a plurality of first meander patterns extending in a first direction and a plurality of second meander patterns extending in a second direction intersecting said first meander patterns to define a plurality of enclosed cells, said meander patterns adapted so that said stent prior to expansion is substantially uniformly flexible along its longitudinal axis and bendable in substantially any direction and in several directions at once without affecting the structural or functional integrity of said stent, said first and said second meander patterns disposed and adapted to cooperate so that upon the expansion of said stent said first meander patterns and said second meander patterns change shape to compensate for the tendency of said stent to foreshorten when said stent is expanded, said meander patterns further adapted to impart rigidity to said stent in an amount sufficient to support a lumen when said stent is expanded.

41. An expandable stent, including:
a plurality of connected cells defining a longitudinal aperture having a longitudinal axis, said cells arranged in a plurality of bands, each of said plurality of cells in each of said bands comprising:
a) a first member having a first end and a second end;
b) a second member having a first end and a second end,
c) a third member having a first end and a second end;
d) a fourth member having a first end and a second end;
e) a first loop defining a first angle disposed between said first end of said first member and said first end of said second member;
f) a second loop defining a second angle disposed between said second end of said third member and said second end of said fourth member;
g) a first flexible arcuate compensating member disposed between said second end of said first member and said first end of said third member; and
h) a second flexible arcuate compensating member disposed between said second end of said second member and said first end of said fourth member, said first flexible arcuate compensating member and said second flexible arcuate compensating member of each of said plurality of cells in each of said plurality of bands flexibly connecting adjacent bands.

42. The stent of claim 41 wherein said first and said second flexible arcuate compensating members are adapted to lengthen upon the expansion of said stent to compensate for the tendency of said stent to foreshorten when said stent is expanded.

43. The stent of claim 41, wherein said first and said second flexible arcuate compensating members are readily differentially compressible or expandable when said stent is unexpanded and are less differentially compressible or expandable after said stent is expanded.

44. The stent of claim 41, wherein said first and said second flexible arcuate compensating members are provided with a width that is smaller than the width of said first, said second, said third, and said fourth members and said first loop and said second loop.

45. The stent of claim 42 wherein said first and said second flexible arcuate compensating members elongate in an amount substantially equal to the amount that the distance between the ends of said first and second members and said third and fourth members increases when said stent is expanded by a catheter balloon.

46. A stent formed of a tube having a patterned shape, the patterned shape comprising:
first meander patterns which are periodic about axes extending in a first direction;
second meander patterns which are periodic about axes extending in a second direction different than said first direction, wherein said second meander patterns are intertwined with said first meander patterns; and
wherein said second meander patterns define a plurality of flexible arcuate compensating members adapted to elongate in said second direction to compensate for the tendency of said first meander patterns to foreshorten when said stent is expanded.

47. A generally longitudinally extending tubular stent which is substantially uniformly flexible with respect to its longitudinal axis by the flexibility of its cells with respect to said axis including:
(a) a plurality of cells flexible around said longitudinal axis connected to one another about the circumference of said stent to form a band of flexible cells, each of said flexible cells having apices disposed apart and generally opposite to one another,
(b) each of said flexible cells having a plurality of flexible links disposed apart and generally opposite to one another,
(c) each of said flexible links including a plurality of portions with neighboring portions having an area of inflection therebetween, and
(d) said flexible cells in said adjacent bands of flexible cells connected to one another.

48. An expandable stent, including:
a plurality of connected cells having a longitudinal axis defining a structure of flexible cells having a longitudinal axis and a circumferential axis substantially perpendicular to said longitudinal axis;
each of said flexible cells having apices disposed apart and generally opposite to one another along said longitudinal axis of each of said cells;
each of said flexible cells having at least two flexible links disposed apart and generally opposite to one another about the circumferential extension of the cell, each of said flexible links including at least two portions with an area of inflection therebetween.

49. An expandable stent having a longitudinal axis, comprising:
a plurality of flexible cells having a first and a second end, said cells disposed about the circumference of the stent, each of said cells comprising:
a first pair of members connected by an area of inflection generally disposed at said first end of said cell;
a second pair of members connected by an area of inflection generally disposed at said second end of said cell; and
a plurality of flexible links connecting said first and second pair of members and generally disposed between each neighboring cell about the circumference of said stent.

50. The stent of claim 49, wherein said flexible links have some area with a width smaller than the width of said areas of inflection.

51. A generally longitudinally extending tubular stent which is substantially uniformly flexible with respect to its longitudinal axis, said stent consisting essentially of: a plurality of flexible cells, each having a longitudinal extension parallel to said longitudinal axis and a circumferential extension parallel to an arc of a circle around the circumference of the stent,
   (a) wherein each of said flexible cells comprises apices disposed apart and generally opposite to one another along said longitudinal extension of the cell,
   (b) wherein each of said flexible cells comprises at least first and second flexible links, wherein prior to expansion of the stent, the first and second flexible links are disposed apart and generally opposite to one another along the circumferential extension of the cell, and
   (c) wherein each of said flexible links comprises a first attachment point and a second attachment point, the first and second attachment points being on a line segment that extends substantially parallel to said longitudinal axis prior to expansion of the stent, wherein each of said flexible links has a bend in it such that the length of said flexible link is greater than the distance between said first and second attachment points, whereby the flexible link can change shape to allow the distance between the attachment points to become longer or shorter to facilitate bending of the stent.

52. A stent formed of a tube having a patterned shape, the patterned shape comprising;
   even first meander patterns having axes extending in a first direction;
   odd first meander patterns, also having axes extending in said first direction, wherein said odd first meander patterns are 180° out of phase with said even first meander patterns and occur between every two even first meander patterns;
   second meander patterns having axes extending in a second direction, wherein said second meander patterns are intertwined with said even and odd first meander patterns to form a distributed structure;
   wherein said second meander patterns have two loops per period; and
   wherein said even and odd first meander patterns are connected on first and second sides, respectively, of each loop.

53. A stent having a longitudinal axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns; and
   f. wherein said loops are disposed and adapted to cooperate so that upon the expansion of said stent the growth of some of said loops in the longitudinal direction of said tube compensates for the shrinkage of other of said loops in the longitudinal direction of said tube to eliminate any significant shrinkage of said stent in the length during expansion.

54. A stent having a longitudinal axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said meander patterns are disposed and adapted to cooperate so that upon the expansion of said stent the vertical growth of said first meander patterns compensates for the vertical shrinkage of said second meander patterns to eliminate any significant shrinkage of said stent in length during expansion.

55. A stent having a longitudinal axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said loops and meander patterns are disposed and adapted to cooperate so that upon the expansion of said stent the growth of some of said loops in the longitudinal direction of said tube compensates for the shrinkage of other of said loops in the longitudinal direction of said tube to eliminate any significant shrinkage of said stent in the length during expansion.

56. A stent formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said loops are disposed and adapted to cooperate so that upon the bending of said stent the inside curvature is shortened with respect to the outside curvature and said loops change shape to compensate for the difference in length between the inside and outside curvature.

57. A stent formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said stent can bend in any direction and in more than one direction at any time prior to expansion and wherein changes in the shape of said loops upon expansion provides rigidity to said stent to enable said stent to maintain a blood vessel or a lumen at a desired inner diameter.

58. A stent having a longitudinal axis and a vertical axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said loops are disposed and adapted to cooperate so that upon the expansion of said stent the vertical growth of the said loops disposed on said first meander patterns substantially compensates for the vertical shrinkage of said loops disposed on said second mender patterns.

59. A stent having a longitudinal axis and a vertical axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said first and said second meander patterns are disposed and adapted to cooperate so that upon the expansion of said stent the vertical growth of said first meander patterns substantially compensates for the vertical shrinkage of said second meander patterns.

60. A stent having a longitudinal axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said loops disposed on said first meander patterns and said loops disposed on said second meander patterns are disposed and adapted to cooperate so that upon the expansion of said stent said loops change shape to compensate for the tendency of said stent to foreshorten when said stent is expanded.

61. A stent having a longitudinal axis and a vertical axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;
   d. wherein said first meander patterns are spaced apart to leave a portion of said second meander patterns between each pair of adjacent first meander patterns;
   e. wherein each of said second meander patterns has at least one loop between at least one pair of adjacent first meander patterns, and
   f. wherein said first and said second meander patterns are disposed and adapted so that said stent prior to expansion is substantially uniformly flexible along said longitudinal axis and bendable in substantially any direction and in several directions at once without affecting the structural or functional integrity of said stent, said first and said second meander patterns disposed and adapted to cooperate so that upon the expansion of said stent the vertical growth of said first meander patterns substantially compensates for the vertical shrinkage of said second meander patterns, said meander patterns further adapted to impart rigidity to said stent in an amount sufficient to support a lumen when said stent is expanded.

62. A stent having a longitudinal axis and a vertical axis formed of a tube having a patterned shape, the patterned shape comprising:
   a. first meander patterns having axes extending in a first direction;
   b. second meander patterns having axes extending in a second direction, different than said first direction, wherein said second meander patterns intersect with said first meander patterns;
   c. wherein said first meander patterns have loops;

d. wherein said first meander patterns are spaced apart to leave a portion of said second meander patterns between each pair of adjacent first meander patterns;

e. wherein each of said second meander patterns has at least one loop between at least one pair of adjacent first meander patterns, and f. wherein said loops are disposed and adapted so that said stent prior to expansion is substantially uniformly flexible along said longitudinal axis and bendable in substantially any direction and in several directions at once without affecting the structural or functional integrity of said stent, said loops disposed and adapted to cooperate so that upon the expansion of said stent the vertical growth of said loops disposed on said first meander patterns substantially compensates for the vertical shrinkage of said loops disposed on said second meander patterns, said loops further disposed and adapted to impart rigidity to said stent in an amount sufficient to support a blood vessel or lumen when said stent is expanded.

63. A stent having a longitudinal axis formed of a tube having a patterned shape, the patterned shape comprising:

a. first meander patterns having axes extending in a first direction;

b. second meander patterns having axes extending in a second direction, different than said first direction, wherein said second meander patterns intersect with said first meander patterns;

c. wherein said first meander patterns have loops;

d. wherein said first meander patterns are spaced apart to leave a portion of said second meander patterns between each pair of adjacent first meander patterns;

e. wherein each of said second meander patterns has at least one loop between at least one pair of adjacent first meander patterns, and f. wherein said stent is adapted so that when it is expanded radially, its overall length remains substantially the same because some elements of said stent grow in said tube's longitudinal direction while some elements of said stent shrink in said tube's longitudinal direction.

64. A stent formed of a tube having a patterned shape, the patterned shape comprising:

a. first meander patterns having axes extending in a first direction;

b. second meander patterns having axes extending in a second direction, different than said first direction, wherein said second meander patterns intersect with said first meander patterns;

c. wherein said first meander patterns have loops;

d. wherein said first meander patterns are spaced apart to leave a portion of said second meander patterns between each pair of adjacent first meander patterns;

e. wherein each of said second meander patterns has at least one loop between at least one pair of adjacent first meander patterns, and f. wherein at least one of said loops is provided with a width that is smaller than the width of the meander pattern on which said at least one of said loops is disposed.

* * * * *

UNITED STATES PATENT AND TRADEMARK OFFICE
CERTIFICATE OF CORRECTION

PATENT NO.  : 5,972,018
DATED       : October 26, 1999
INVENTOR(S) : Israel et al.

It is certified that error appears in the above-identified patent and that said Letters Patent is hereby corrected as shown below:

Claim 1
Line 15, "comprises" should be -- comprise --.

Claim 2
Line 7, "flat" should be -- first --;
Line 12, "pattern" should be -- patterns --;
Line 13, "pattern;" should be -- patterns; --.

Claim 12,
Line 2, "provides" should be -- provide --.

Claim 17,
Line 3, "cells to" should be -- cells adapted to --.

Claim 30,
Line 3, " ; " should be -- , --.

UNITED STATES PATENT AND TRADEMARK OFFICE
CERTIFICATE OF CORRECTION

PATENT NO. : 5,972,018
DATED : October 26, 1999
INVENTOR(S) : Israel et al.

It is certified that error appears in the above-identified patent and that said Letters Patent is hereby corrected as shown below:

Claim 31,
Line 12, "areas" should be -- area --;
Lines 12-13, "inflection define" should be --inflection, and wherein said first and second areas of inflection define --

Claim 32,
Line 6, "there between" should be -- therebetween --.

Claim 41,
Line 7, " , " should be -- ; --.

Signed and Sealed this

Thirty-first Day of July, 2001

*Attest:*

NICHOLAS P. GODICI
*Attesting Officer*    *Acting Director of the United States Patent and Trademark Office*